United States Patent [19]

Walker

[11] Patent Number: 4,475,080

[45] Date of Patent: Oct. 2, 1984

[54] MICROWAVE MOISTURE MEASUREMENT OF MOVING PARTICULATE LAYER AFTER THICKNESS LEVELING

[76] Inventor: Charles W. E. Walker, 591 W. 57th Ave. #301, Vancouver, British Columbia, Canada

[21] Appl. No.: 376,624

[22] Filed: May 10, 1982

[51] Int. Cl.³ ............................................. G01R 27/04
[52] U.S. Cl. ............................................... 324/58.5 A
[58] Field of Search ............... 324/58.5 A, 61 R, 61 P, 324/65 R, 65 P

[56] References Cited

U.S. PATENT DOCUMENTS

| | | | |
|---|---|---|---|
| 3,460,030 | 8/1969 | Brunton et al. | 324/58.5 |
| 3,693,079 | 9/1972 | Walker | 324/58.5 A |

FOREIGN PATENT DOCUMENTS

| | | | |
|---|---|---|---|
| 665303 | 6/1963 | Canada | 324/61 P |
| 967351 | 5/1975 | Canada | 324/65 |
| 331333 | 7/1930 | United Kingdom | 324/61 P |
| 827004 | 1/1960 | United Kingdom | 324/61 P |
| 1166536 | 10/1969 | United Kingdom | 324/61 P |
| 890208 | 12/1981 | U.S.S.R. | 324/65 R |

*Primary Examiner*—Stanley T. Krawczewicz
*Attorney, Agent, or Firm*—Klarquist, Sparkman, Campbell, Leigh & Whinston

[57] ABSTRACT

Apparatus is disclosed for measuring the moisture content of a moving layer of particulate material carried on a conveyor by transmitting a beam of microwave radiation through such layer. A portion of such microwave beam is absorbed by the water in the particles and the unabsorbed portion is detected to determine the moisture content. A layer leveling means including a rotating endless flexible leveling belt engaged by a pressure roller, contacts the top surface of the particulate layer to level the thickness of such layer upstream of the measuring position, thereby enabling more accurate measurement of its moisture content. The height of the pressure roller above the conveyor is adjusted in response to changes in the thickness of the layer being measured. A beam of penetrating radiation of a type diverse from microwaves, such as gamma radiation, which is absorbed by the total mass of the particulate material may also be employed for determining such mass so that the percent of moisture content can be calculated. The thickness of the measured portion of the layer is determined by measuring the height of the pressure roller above the conveyor. This height measurement may be made by an ultrasonic distance gauge, or by a electro-mechanical transducer moved with the height adjustment of the pressure roller.

17 Claims, 7 Drawing Figures

MICROWAVE MOISTURE MEASUREMENT OF MOVING PARTICULATE LAYER AFTER THICKNESS LEVELING

BACKGROUND OF INVENTION

The subject matter of the present invention relates generally to apparatus for measuirng the moisture content of particulate material in a moving particulate layer carried on a conveyor by transmitting a beam of microwave radiation through such layer so that a portion of such beam is absorbed by such moisture. More particularly, the invention relates to such an apparatus employing an improved leveling means for leveling the thickness of the particulate layer prior to measurement of the moisture content. Preferably, the leveling means of the present invention includes a rotating endless, flexible leveling belt and a pressure roller which urges the leveling belt into contact with the top surface of the layer of particulate material to level such surface laterally across the layer. The height of the pressure roller and leveling belt above the conveyor may be adjusted in response to changes in the thickness longitudinally along the particulate layer. A beam of penetrating radiation diverse from microwaves, such as gamma radiation, which is absorbed by the total mass of the particulate material may also be transmitted through the measured portion of the particulate layer in order to determine the mass of such layer so that the percent of moisture content may be calculated. The source or detector of the microwaves and/or penetrating radiation may be positioned within the leveling belt to provide a more compact measurement apparatus.

Previously it has been proposed in U.S. Pat. No. 3,460,030 issued Aug. 5, 1969 to Brunton et al and my earlier U.S. Pat. No. 3,693,079 issued Sept. 19, 1972 to Walker to provide an apparatus for measuring the percent moisture content of particulate material using beams of microwaves and penetrating radiation, including gamma rays. However, these prior art apparatus were not completely successful because of their inability to maintain the measured particulate layer with a sufficiently uniform predetermined thickness. Thus, the leveling rake means and the leveling roller means of U.S. Pat. No. 3,693,079 have not proved satisfactory in leveling the particulate layer for certain applications of such apparatus because they do not contact a sufficiently large area of such layer.

SUMMARY OF INVENTION

One object of the present invention is to provide an improved microwave apparatus for measuring the moisture content of a moving layer of particulate material whose thickness is leveled for more accurate measurement of moisture by contacting the layer with a leveling means over a large area.

Another object of the invention is to provide such a microwave moisture measurement apparatus in which the surface of the layer of particulate material is smoothed into a flatter layer of more uniform thickness laterally across the layer by an improved leveling means including an endless leveling belt which is pressed into engagement with the top surface of such layer.

A further object of the invention is to provide such a microwave moisture measurement apparatus in which the leveling means is adjustable in height above the conveyor to enable the measurement of a particulate layer of different thickness longitudinally along the layer.

An additional object of the invention is to provide such a microwave moisture measurement apparatus of compact size in which the source or detector of the microwave radiation is positioned within the endless leveling belt.

Still another object of the invention is to provide such a microwave moisture measuring apparatus which accurately measures the percent of moisture content of the particulate material by also transmitting a beam of penetrating radiation diverse from such microwaves, such as gamma rays, in order to determine the mass of such particulate layer in a more accurate manner by leveling the measured portion of the layer to provide a more uniform thickness.

A still further object of the invention is to provide such a microwave moisture measurement apparatus in which the leveling means includes a pressure roller which engages the leveling belt to urge it into contact with the top surface of the particulate layer so that the thickness of such layer is determined by the height of the pressure roller above the conveyor belt to more esily determine the percent moisture content of the measured portion of such layer.

DESCRIPTION OF DRAWINGS

Other aspects and advantages of the present invention will be apparent from the following drawings and description of a preferred embodiment thereof.

DESCRIPTION OF PREFERRED EMBODIMENT

Figure 1:
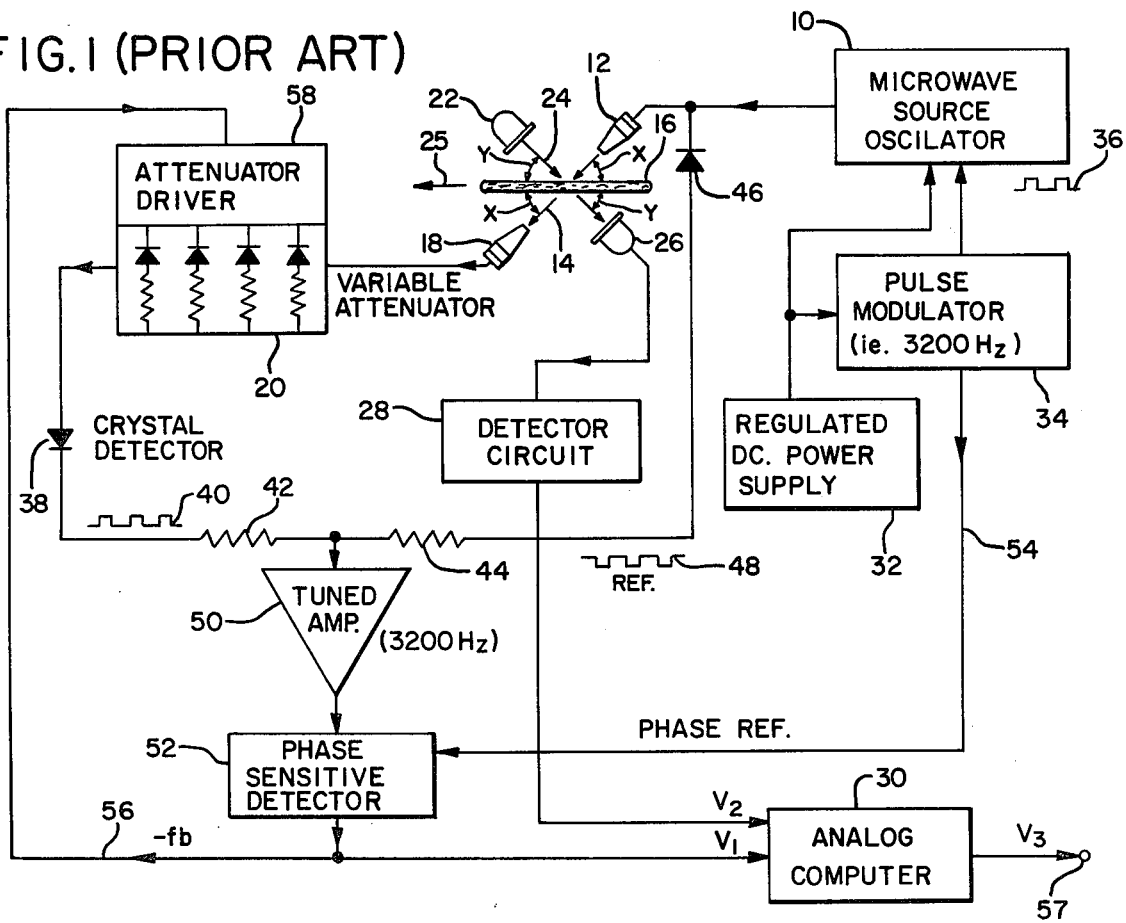
FIG. 1 is a schematic diagram of a prior art microwave moisture measurement system to which may be added the particulate layer leveling means of the present invention.

As shown in FIG. 1, it has been previously proposed in my earlier U.S. Pat. No. 3,693,079 to provide a system for measuring the percent of moisture content of particulate material, such as wood chips, foundry sand, cereal grain or coal dust, using a beam of microwaves and a beam of penetrating radiation of a diverse type, such as gamma rays. In this prior art system, a microwave oscillator 10 producing a microwave signal having a frequency in the range of about 1 to 30 gigahertz depending on the size of the particulate material, is connected at its output to a microwave source antenna 12. The antenna 12 radiates a beam 14 of microwaves through a layer 16 of particulate material whose moisture content is being measured, to a microwave receiving antenna 18. The output of the antenna 18 is transmitted through a variable microwave attenuator 20 to produce at the output of such attenuator an electrical signal corresponding to the received portion of the microwave beam 14 which is transmitted through the layer 16. Another portion of the microwave beam 14 is absorbed by the water in the particulate layer 16 which is present as moisture absorbed in the particulate material. Water has a microwave resonance frequency of 22 gigahertz so it will absorb microwaves in the range of 1 to 30 gigahertz of beam 14. Thus, the power level of the microwave beam received by the receiving antenna 18 is related to the moisture content of the particulate layer 16.

A source 22 of penetrating radiation diverse in type from microwaves, which is absorbed by the total mass of the particulate material including the water contained therein, emits a beam 24 of such penetrating radiation through the particulate layer 16. The penetrating radiation of beam 24 may be X-rays, gamma rays, beta rays or high energy electrons. The unabsorbed portion of beam 24 is transmitted to a radiation detector 26 which produces an electrical signal that is related to the mass of the particulate material in the measured portion of the layer 16. It should be noted that the particulate layer 16 is conveyed in the direction 25 at a high speed of, for example 400 feet per minute, by supporting such layer on a moving endless conveyor belt. The mass measurement signal output of the penetrating radiation detector 26 is transmitted through a detector circuit 28 to apply a D.C. output voltage $V_2$ corresponding to such mass signal to one input of an analog computer 30 which is employed to calculate the percentage moisture content of the particulate layer 16, and may be the analog computer shown in U.S. Pat. No. 3,693,079. It should be noted that the axis of the microwave beam 14 and the axis of the beam 24 of penetrating radiation intersect at a point within the moving particulate layer 16. The point of intersection of the two beams 14 and 24 is in the middle of a measured portion of the particulate layer 16, such measured portion moving along the length of the layer as such layer is conveyed in direction 25 by the conveyor belt on which it is supported.

In order to prevent microwaves reflected from the upper and lower surfaces of the particulate layer 16 from striking either of the antennas 12 or 18 to produce standing waves, the microwave beam 14 is directed at an acute angle X of between about 40° to 65° with respect to the plane of the upper surface of the particulate layer. This prevents the distortion of the microwave moisture measurement which can be caused by such microwave reflections when they produce standing waves due to multiple reflections between the layer and the antenna, such as are produced when the beam is perpendicular to the layer. The beam 24 of gamma rays or other penetrating radiation also extends at an acute angle Y to the plane of the top surface of layer 16. The angle Y is approximately equal to the angle X so that the beam 24 has the same path length through such layer as the microwave beam 14.

A regulated power supply 32 of approximately +8 volts D.C. is applied to the microwave oscillator 10 and a pulse modulator 34 source of an audio frequency square wave signal 36 of about 3200 hertz. The output signal 36 of the pulse modulator is applied to the oscillator 10 in order to amplitude modulate the high frequency (1 to 30 gigahertz) oscillator sinewave signal at an audio frequency of 3200 hertz. The amplitude modulated received signal is transmitted from attenuator 20 through a crystal detector 38 which rectifies the corresponding electrical signal to produce a detected signal 40. This detected signal 40 is transmitted through a comparator resistor 42 for comparison with a constant voltage amplitude reference signal of the same frequency transmitted through another comparator resistor 44 connected in series with resistor 42. The reference signal is obtained by another crystal detector 46 connected at its cathode to the output of the microwave oscillator 10 and at its anode to the other end of the resistor 44, such reference signal 48 having the same frequency as the received signal 40, but of a constant amplitude. The voltage amplitude difference signal produced at common terminal of resistors 42 and 44 is transmitted to the input of a tuned amplifier 50 having a narrow frequency band width tuned to approximately 3200 hertz in order to reduce noise. The output of the tuned amplifier 50 is connected to one input of a phase sensitive detector 52 whose phase reference input 54 is connected to the output of the phase modulator 32. The phase sensitive detector produces a D.C. output signal $V_1$ whose voltage is proportional to the moisture content of the particulate layer 16.

The voltage $V_1$ is transmitted through a negative feedback conductor 56 to the input of an attenuator driver 58 which causes attenuator 20 to attenuate the microwaves received from antenna 18 until they reach a power level of the proper value to produce a detected signal 40 of constant predetermined amplitude. The attenuator driver 58 may be an electric motor for rotating a microwave cutoff valve, such as a rotary vane, when such valve is used as a mechanical variable attenuator 20. However, the attenuator 20 may also be an electronic attenuator of a PIN diode type, which causes the microwave attenuation to vary directly in accordance with a D.C. biased current supplied to the PIN semiconductor diodes which act as variable resistors between the conductors of a high frequency transmission line. In this case, the attenuator driver 58 includes a function generator which will supply the required bias current to the PIN diodes under the control of the feedback voltage $V_1$.

The moisture measurement voltage $V_1$ is applied to one input of the analog computer 30. The other input to such computer is a voltage $V_2$ produced by the output of the detector circuit 28 corresponding to the total mass of the measured portion of the particulate layer 16 including the mass of the solid particulate material and absorbed water as measured by the beam 24 of penetrating radiation. The output 57 of the analog computer is a voltage $V_3$ which corresponds to the percent moisture content of the particulate layer 16. The operation of the microwave moisture measuring system of FIG. 1 including computer 30 is more completely described in U.S. Pat. No. 3,693,079.

Figure 2:
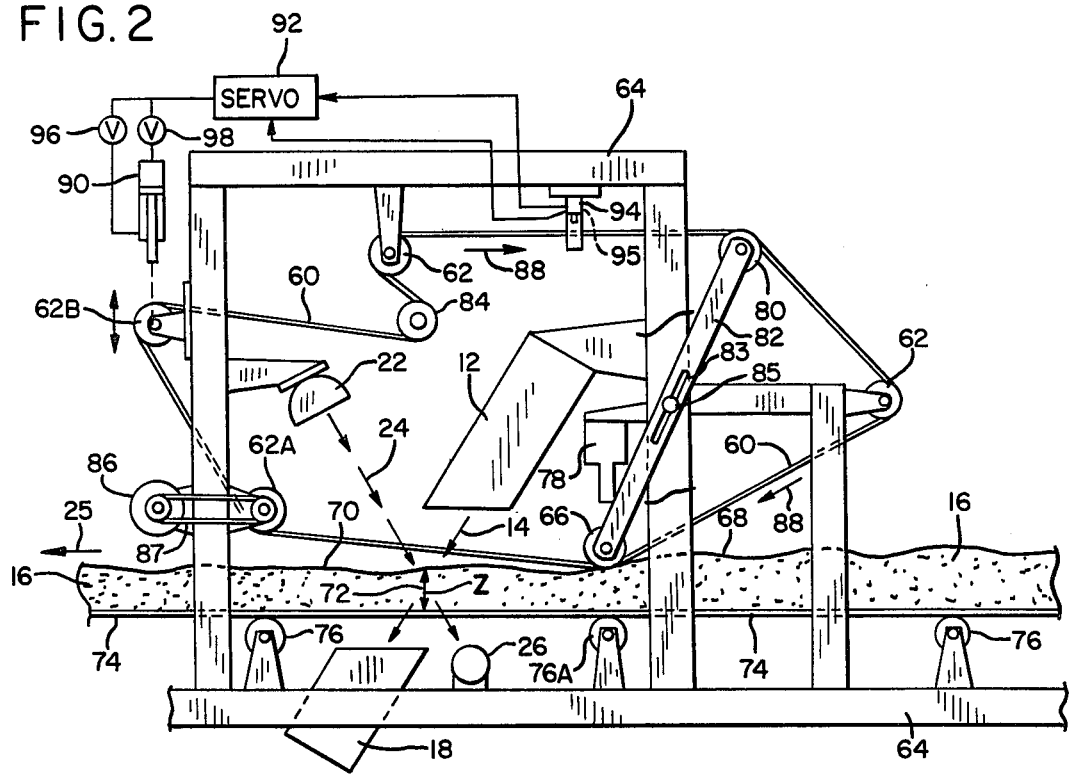
FIG. 2 is a side elevation view of one embodiment of the microwave moisture measurement apparatus of the present invention including such particulate layer leveling means.

As shown in FIG. 2 a microwave moisture measurement apparatus in accordance with the present invention which may be used in the system of FIG. 1 includes an endless, flexible leveling belt 60 which moves about guide rollers 62 which are fastened to the frame 64 of such apparatus. In addition, a pressure roller 66 is positioned in contact with top side of the lower reach of the leveling belt to urge such belt into contact with the upper surface 68 of the particulate layer 16 in order to smooth and flatten such surface into a leveled surface 70 which is flattened in a transverse direction laterally across the layer. This leveling forms the layer 16 with a substantially uniform predetermined thickness Z laterally across the layer at the measuring position 72 where the layer is intersected by the microwave beam 14 and the beam 24 of penetrating radiation.

Figure 4:
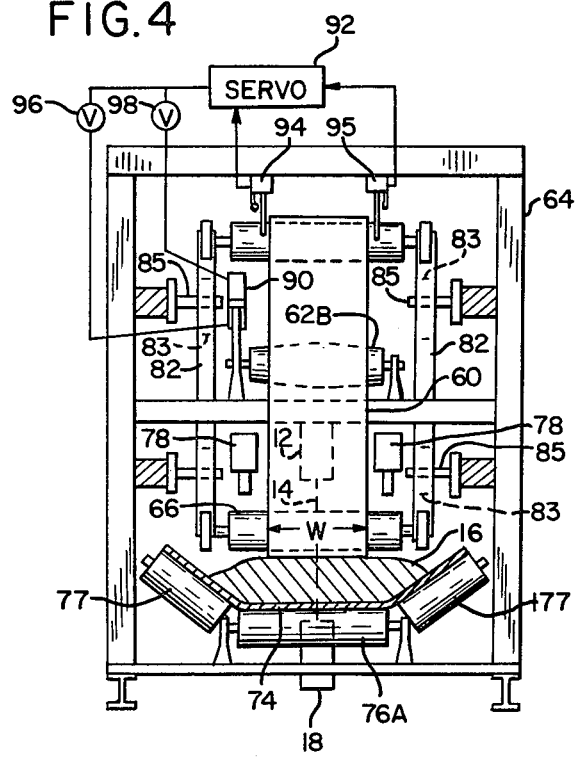
FIG. 4 is a vertical section view taken along the line 4—4 of FIG. 3.

The particulate layer 16 is carried on an endless conveyor belt 74 which is mounted on support rolls 76 and 77, including bottom support rolls 76 and side support rolls 77 sloping upward at an angle of about 45° to the axis of rolls 77 to bend the side portion of the belt 74 upward thereby maintaining layer 16 on such conveyor belt, as shown in FIG. 4. A bottom support roll 76A is positioned immediately beneath the pressure roller 66 of the leveling belt 16 so that the distance between the pressure roller 66 and the support roll 76A indicates the thickness Z of the leveled particulate layer 26 at the measuring position 72. Thus, the height of the pressure roller 66 above the conveyor belt 74 less the thickness of the leveling belt 60 equals the thickness of the measured portion of the particulate layer. The height of the pressure roller 66 may be measured by an ultrasonic distance gauge 78 which radiates a beam of high frequency sound waves at the surface of the pressure roller and receives reflected sound waves therefrom to generate an electrical signal which corresponds to the distance between such gauge and such roller and is proportional to the height of the pressure roller above the conveyor belt. The ultrasonic gauge 78 may be replaced by an electrical-mechanical transducer which is coupled to the pressure roller 66 for movement therewith during adjustment of the height of such roller. For example, the movable contact of a variable resistance potentiometer coupled to movement of the pressure roller may be employed as such transducer.

It should be noted that the microwave source antenna 18 and the gamma ray source 22 are both positioned within the endless leveling belt 60 for a more compact apparatus. Alternatively, it is possible that the detectors 18 and 26 can be positioned within the endless leveling belt 60 in which case the sources 12 and 22 would be positioned below the conveyor belt 74.

Assuming that the density of the particulate material in layer 16 is constant then the thickness of the measured portion of the particulate layer can be used to calculate the mass of such layer without using the beam 24 of penetrating radiation while moisture content is measured by the microwave beam 14. Then the height measurement of the pressure roller can be used as an indication of mass of the measured portion of layer 16. This is possible when the particulate material being measured is powdered coal. In this case, the beam of penetrating radiation 24, the source 22 and the detector 26 may be eliminated. However, this may not be possible for the moisture measurement of other particulate material whose density varies such as by wood chips.

The ends of pressure roller 66 may be connected to the ends of a second roller 80 engaging the upper reach of the leveling belt 60, by a pair of mechanical links 82, each having a slot 83 which engages a pin 85 extending from a vertical beam portion of the frame 64. As a result, vertical adjustments of the height of the pressure roller 66 due to changes in the thickness of the layer 16 of particulate material are accomplished by sliding the link slots 83 relative to pins 85. These height adjustments are compensated by corresponding vertical adjustments of the second roller 80 in order to maintain the path length of the leveling belt 60 constant so that the belt is kept at the proper tension. A tension adjust roller 84 may, also, be provided for minor adjustments in the tension of the endless belt 60 such as when slack develops due to stretching or wear. The tension adjust roller is spring mounted in a conventional manner for automatic adjustment of the tension when slack develops.

The leveling belt 60 may be an idler belt which moves only by contact with the layer 16 in the same direction as the conveyor belt 74, but may move at a slower speed as a result of suitable braking of such leveling belt. However, it is more preferable to drive such leveling belt in the same direction as the conveyor belt, but at a slightly slower speed by means of an electric motor 86. Motor 86 is mounted on the frame 64 and has its output shaft coupled by a coupling chain 87 or other coupling to a drive roll 62A so that the leveling belt is driven in a direction 88 which is the same as the direction 25 of the movement of the layer 16. This motor driven movement of the leveling belt 60 provides more efficient leveling of the layer. In some cases the leveling belt tends to slide sideways off the rollers and some of the rolls 62 may be crowned with larger diameters in their central portion than their ends to prevent this. Also, one of the belt rolls 62B may be tilted vertically adjustable by a servo-controlled positioner, such as a cylinder 90 whose piston rod is connected to one end of the shaft of such roll, and a servo motor 92 controlled by a pair of belt position sensor switches 94 and 95 on opposite sides of the leveling belt. The two switches when closed cause the servo motor to rotate in opposite directions so that such motor opens and closes two valves 96 and 98 connected to the opposite ends of cylinder 90 to move its piston and end of roll 62B up or down for automatic belt alignment.

Figure 3:
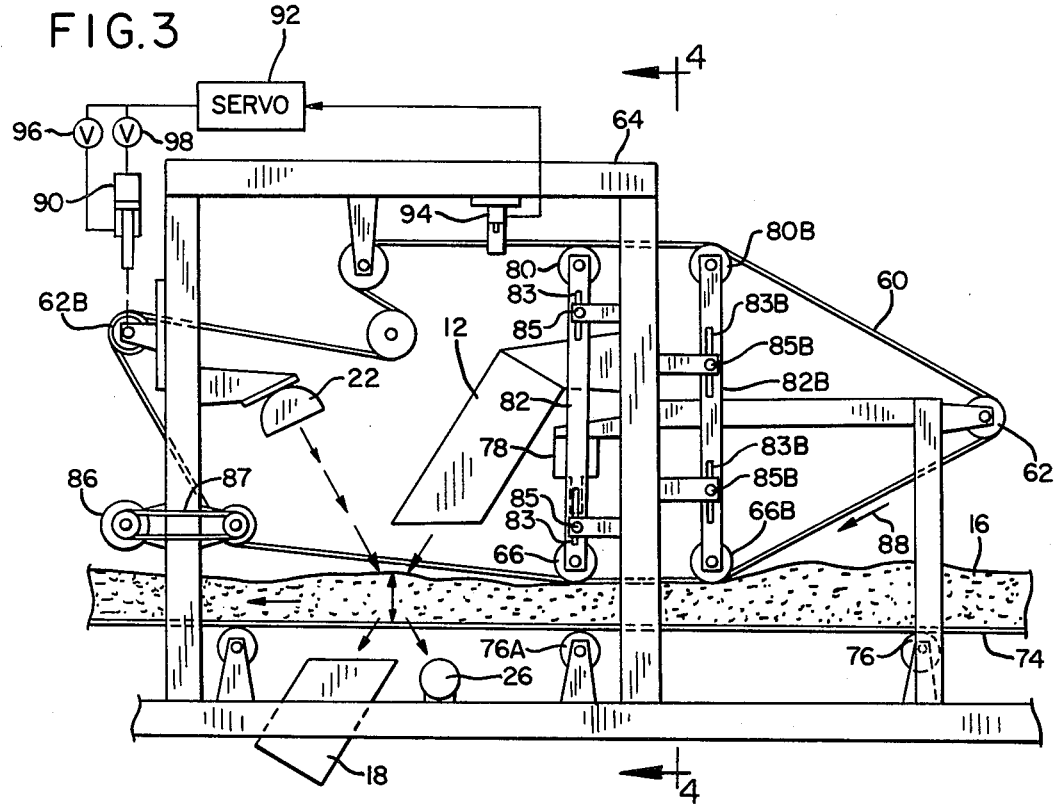
FIG. 3 is a side elevation view of another embodiment of the present invention.

If this is not sufficient a second pressure roller 66B may be added upstream of roller 66 along with a second pair of links 82B and upper rollers 80B, as shown in FIGS. 3 and 4, to increase the area of contact between the leveling belt and the layer, such second roller being positioned at a slightly greater height than roller 66. Also, it may be desirable to provide a herringbone pattern to the bottom surface of the leveling belt 60 for even more efficient leveling.

Figure 5A:
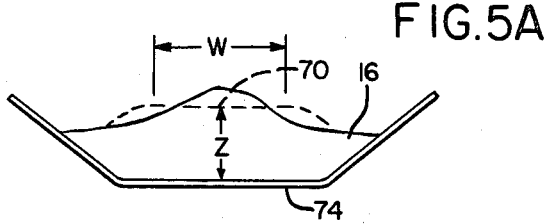
FIGS. 5A, 5B, 5C are cross-section views through the layer of particulate material to show different leveling conditions.

As shown in FIG. 5A, in most cases the particulate layer 16 is flatend by the leveling belt 60 to provide a substantially horizontal surface 70 on the central portion, W, of such layer contacted by such belt which is of substantially uniform thickness, Z, laterally across such layer. However, even under the condition shown in FIG. 5A the thickness of the layer 16 may vary longitudinally along such layer after leveling. This does not matter as long as the thickness, Z, at the measuring position 72 during moisture and mass measurements by beams 14 and 24 is known from the height measurements of the distance gauges 78 and the speed of the conveyor 74.

Figure 5B:
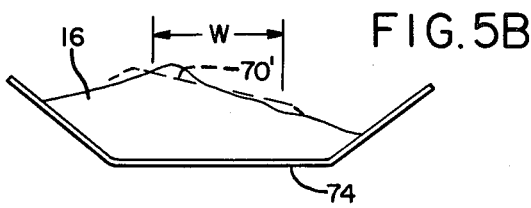
Figure 5C:
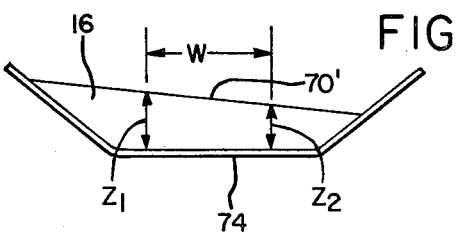

However, in some cases shown in FIGS. 5B and 5C, such as when the layer 16 is non-symmetrical, it is flatened by the leveling belt 60 into an inclined surface 70' which is not of uniform transverse thickness. Instead, the thickness of the inclined surface 70' varies from a maximum thickness, $Z_1$, to a minimum thickness, $Z_2$, at the opposite sides of the central portion, W, of the layer contacted by the leveing belt. These thicknesses $Z_1$ and $Z_2$ are each measured by a different one of the pair of ultrasonic distance gauges 78 positioned above the opposite ends of the pressure roller 66, as shown in FIG. 4. Then the average thickness, Z, of the inclided surface 70' is determined by $Z=\frac{1}{2}(Z_1+Z_2)$ and used to calculate the moisture content. It should be noted that the pressure rollers 66 and 66B are mounted on links 82 and 82B so that the opposite ends of their shafts can be independently adjusted in height to tilt such rollers to follow the inclined surface 70' of the layer under the conditions of FIGS. 5B and 5C.

It will be obvious to those having ordinary skill in the art that many changes may be made in the above-described invention. Therefore, the scope of the invention should only be determined by the following claims.

I claim:

1. Apparatus for measuring the moisture content of particulate material, comprising:
   conveyor means for conveying a layer of particulate material containing water absorbed in said material;
   microwave beam radiation means for directing a beam of microwaves through a measured portion of said layer from a microwave source to a microwave detector separated by the conveyor means which conveys said layer through a measuring position between said source and said detector, said beam of microwaves being absorbed a greater amount by the water in said layer than by the solid particulate material, and said detector detecting the portion of said microwave beam which is transmitted through said layer to produce an electrical signal which is proportional to the amount of water in the measured portion of said layer;
   leveling means for leveling said layer of particulate material to produce a layer of predetermined thickness at said measuring position, said leveling means including a rotating endless, flexible leveling belt whose lower side contacts the top surface of said layer and which is engaged by a pressure roller on the upper side of said belt upstream of said measuring position; and
   adjustment means for adjusting the height of said pressure roller above said conveyor means to change the spacing between the lower side of said belt and the upper surface of said conveyor means which determines the thickness of said layer at said measuring position.

2. Apparatus in accordance with claim 1 in which either the microwave source or the microwave detector is contained within the endless belt.

3. Apparatus in accordance with claim 2 which also includes a source of penetrating radiation of a type diverse from said microwaves which is absorbed in an amount proportional to the total mass of the moist particulate material for directing a beam of said penetrating radiation through said measured portion of said layer and a detector for detecting the transmitted portion of said beam of penetrating radiation to produce another electrical signal proportional to the total mass of the measured portion of said layer.

4. Apparatus in accordance with claim 3 in which the source or detector of penetrating radiation is also contained within the endless belt.

5. Apparatus in accordance with claim 3 in which the penetrating radiation is gamma rays.

6. Apparatus in accordance with claim 1 in which the conveyor means includes a conveyor belt which is substantially flat at said measuring position.

7. Apparatus in accordance with claim 6 in which the conveyor belt passes over a support roll at said measured position which is beneath said pressure roller contacting the leveling belt.

8. Apparatus in accordance with claim 7 which also includes a means for determining the thickness of the measured portion of said layer by the distance between said support roll and said pressure roller.

9. Apparatus in accordance with claim 1 which also includes thickness determination means for measuring the height of the pressure roller above the conveyor means to determine the thickness of the measured portion of said layer.

10. Apparatus in accordance with claim 9 in which the thickness determination means is a pair of ultrasonic distance gauges which measure the heights of both ends of the pressure roll.

11. Apparatus for measuring the moisture content of particulate material, comprising:
    conveyor means for conveying a layer of particulate material containing water absorbed in said material;
    microwave beam radiation means for directing a beam of microwaves through a measured portion of said layer from a microwave source to a microwave detector separated by the conveyor means which conveys said layer through a measuring position between said source and said detector, said beam of microwaves being absorbed a greater amount by water in said layer than by the solid particulate material, and said detector detecting the portion of said microwave beam which is transmitted through said layer to produce an electrical signal which is proportional to the amount of water in the measured portion of said layer;
    leveling means for leveling said layer of particulate material to produce a layer of predetermined thickness at said measuring position, said leveling means including a rotating endless, flexible leveling belt whose lower side contacts the top surface of said layer and which is engaged by a pressure roller on the upper side of said belt upstream of said measuring position;
    adjustment means for adjusting the height of said pressure roller above said conveyor means to change the spacing between the lower side of said belt and the upper surface of said conveyor means which determines the thickness of said layer at said measuring position; and
    thickness measurement means for measuring the thickness of said layer at both ends of said pressure roller after leveling to determine the average thickness of the measured portion of said layer.

12. Apparatus in accordance with claim 11 in which the thickness measurement means includes a pair of ultrasonic distance gauges at the opposite ends of said pressure roll.

13. Apparatus in accordance with claim 11 in which the leveling means includes a compensation means linked to said pressure roller and contacting the leveling belt to maintain the path length of said leveling belt substantially constant in different height positions of said pressure roller.

14. Apparatus in accordance with claim 13 in which the compensation means is an upper roller which contacts the upper reach of said leveling belt and the heights of both the pressure roller and the upper roller are adjusted simultaneously the same amount by a pair of links joining said upper roller to said pressure roller at the ends of their shafts and mounted for vertical sliding movement of said links.

15. Apparatus in accordance with claim 14 which also includes a second pressure roller contacting the leveling belt upstream of the first mentioned pressure roll, said second pressure roller being connected by a second pair of links to a second upper roller contacting said belt.

16. Apparatus in accordance with claim 11 which also includes motor means for moving said leveling belt in a direction opposite to the movement of said layer at said measurement position.

17. Apparatus in accordance with claim 11 which includes an automatic belt aligning means for maintaining the leveling belt on its support rolls comprising belt position sensing switches, servo motor means connected to said sensing switches, and support roll position adjustment means for adjusting the positions of the opposite ends of a support roll in response to the output of said servo motor means to align said leveling belt.

* * * * *